US012728078B2

(12) United States Patent
Saghiri

(10) Patent No.: US 12,728,078 B2
(45) Date of Patent: Sep. 8, 2026

(54) COMPOSITION AND METHOD FOR A ROOT CANAL FILLING

(71) Applicant: Rutgers, The State University of New Jersey, New Brunswick, NJ (US)

(72) Inventor: Mohammad Ali Saghiri, Hackensack, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 844 days.

(21) Appl. No.: 17/711,651

(22) Filed: Apr. 1, 2022

(65) Prior Publication Data

US 2022/0226199 A1 Jul. 21, 2022

Related U.S. Application Data

(63) Continuation of application No. PCT/US2020/053925, filed on Oct. 2, 2020.

(60) Provisional application No. 62/909,623, filed on Oct. 2, 2019.

(51) Int. Cl.

| | |
|---|---|
| ***A61K 6/54*** | (2020.01) |
| ***A61C 5/50*** | (2017.01) |
| ***A61C 5/64*** | (2017.01) |
| ***C08G 18/10*** | (2006.01) |
| ***C08G 18/18*** | (2006.01) |
| ***C08G 18/32*** | (2006.01) |
| ***C08G 18/48*** | (2006.01) |
| ***C08G 18/66*** | (2006.01) |
| ***C08G 18/77*** | (2006.01) |
| ***C08K 3/08*** | (2006.01) |
| ***C08K 3/105*** | (2018.01) |
| ***C08K 3/22*** | (2006.01) |
| ***C08L 75/08*** | (2006.01) |

(52) U.S. Cl.

CPC .................. *A61K 6/54* (2020.01); *A61C 5/64* (2017.02); *C08G 18/10* (2013.01); *C08G 18/1858* (2013.01); *C08G 18/3206* (2013.01); *C08G 18/4833* (2013.01); *C08G 18/6677* (2013.01); *C08G 18/771* (2013.01); *C08K 3/08* (2013.01); *C08K 3/105* (2018.01); *C08K 3/22* (2013.01); *C08L 75/08* (2013.01); *A61C 5/50* (2017.02); *C08K 2003/2244* (2013.01); *C08K 2003/2258* (2013.01); *C08K 2003/2296* (2013.01); *C08K 2201/011* (2013.01)

(58) Field of Classification Search

CPC ..... C08L 75/08; C08G 18/73; C08G 18/3206; C08G 18/4833; C08K 3/08; C08K 3/22; C08K 3/30; C08K 3/105

See application file for complete search history.

(56) References Cited

U.S. PATENT DOCUMENTS

| | | | | |
|---|---|---|---|---|
| 6,207,767 | B1 | 3/2001 | Bennett et al. | |
| 2005/0107868 | A1* | 5/2005 | Nakayama ............ | A61L 27/507 606/151 |
| 2006/0051394 | A1* | 3/2006 | Moore .................... | A61L 31/10 424/423 |
| 2009/0127195 | A1 | 5/2009 | Calabrese et al. | |
| 2009/0175921 | A1* | 7/2009 | Gunatillake ............ | C07C 69/40 252/182.18 |
| 2009/0324675 | A1 | 12/2009 | Gunatillake et al. | |
| 2012/0277844 | A1* | 11/2012 | Wu ......................... | A61L 27/46 623/1.11 |
| 2016/0030625 | A1* | 2/2016 | Mrozek ...................... | C08J 9/28 521/64 |
| 2017/0224476 | A1* | 8/2017 | You ......................... | A61L 27/18 |

FOREIGN PATENT DOCUMENTS

| | | | |
|---|---|---|---|
| CN | 1087662 | A | 1/2000 |
| CN | 1771061 | A | 5/2006 |
| CN | 103013094 | A | 4/2013 |
| WO | 9410259 | A1 | 5/1994 |
| WO | 2004062704 | A1 | 7/2004 |

* cited by examiner

*Primary Examiner* — Kregg T Brooks
(74) *Attorney, Agent, or Firm* — Greenberg Traurig, LLP

(57) ABSTRACT

Compositions and methods for the synthesis of polymer foam materials, wherein the polymer foam materials include expandable polymers, which can be applied to many dental applications, such as for example but not limited to one or more of a filler, a sealer, a filling, and a root canal. The expandable polymers can include a cross linkable material that expands upon crosslinking.

5 Claims, 2 Drawing Sheets

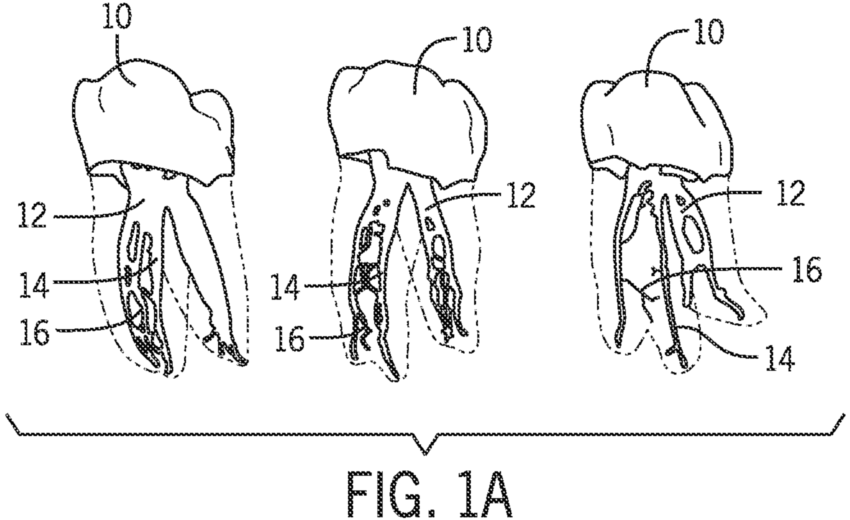
FIG. 1A
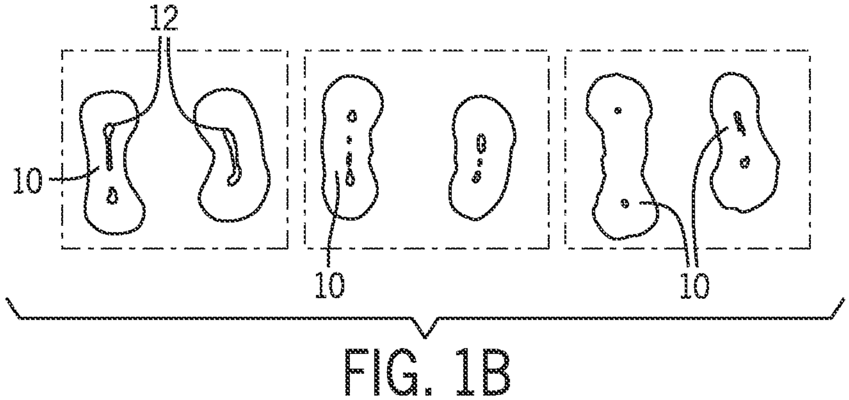
FIG. 1B
FIG. 2

30
42
34
38
32
36
40

50
52
54
56
OBTAIN POLYMER / MONOMER
OBTAIN ISOCYANATE GROUP COMPOUND
MIX TOGETHER

COMPOSITION AND METHOD FOR A ROOT CANAL FILLING

CROSS-REFERENCE TO RELATED APPLICATIONS

This patent application is a Continuation Application relating to and claiming the benefit of commonly-owned, co-pending PCT International Application No. PCT/US2020/053925, filed Oct. 2, 2020, which claims priority to and the benefit of U.S. provisional patent application No. 62/909,623 filed on Oct. 2, 2019, the contents of each of the foregoing are herein incorporated by reference in its entirety.

FIELD

Some embodiments of the present disclosure relate to compositions and methods for use in endodontic treatment and, more particularly, compositions for root canal filling and methods for use of same.

BACKGROUND

Endodontic treatment or root canal therapy (RCT) is a commonly performed tooth treatment in the field of dentistry. Conventionally, RCT is directed towards the treatment of a tooth inner space, which contains a soft tissue known as "dental pulp tissue", and then filling the inner space with biocompatible materials. After the removal of dental pulp from, and after the cleaning, shaping and/or irrigation of, the tooth root canal space, the cleaned, disinfected, and shaped root canal space is dried out and then filled by biocompatible materials.

BRIEF SUMMARY

Some embodiments disclosed herein relate to compositions and methods for the synthesis of polymer foam materials which is biocompatible, and methods for using the polymer foam materials. Some of the embodiments of the polymer foam materials include expandable polymers (including expandable biocompatible polymers), wherein their expansion characteristics are in three dimensions that can be controlled to meet a particular application. Some of the embodiments of the expandable biocompatible polymers can be applied to many dental applications, such as for example but not limited to a filler, a sealer, a filling, a root canal filler, and combinations thereof. Some of the embodiments of the polymer foam materials can be placed in contact with, for example but not limited to, dentin, enamel, etc. In some embodiments, the polymer foam materials can be formed within different tissue conditions, pH, temperature, and level of humidity, such that, for example, the polymer foam material has an improved biocompatible property that does not negatively affect the tissue conditions contacting or near the polymer foam material. For example, some embodiments of the polymer foam materials do not negatively impact the contacting tissue conditions. Examples of negative impact of the contacting tissue conditions include changing (i.e., significantly lowering or raising) one or more of the properties of the tissue, wherein the properties include, but are not limited to, pH, temperature, and level of humidity.

BRIEF DESCRIPTION OF THE DRAWINGS

FIG. 1A shows schematic views of root canal spaces in a tooth, while FIG. 1B shows top cross-sectional views of root canals which illustrate complex and irregular tooth root canal patterns;

FIG. 2 shows a schematic view of filled/obturated tooth root canal spaces;

DETAILED DESCRIPTION

Figures 3, 4:
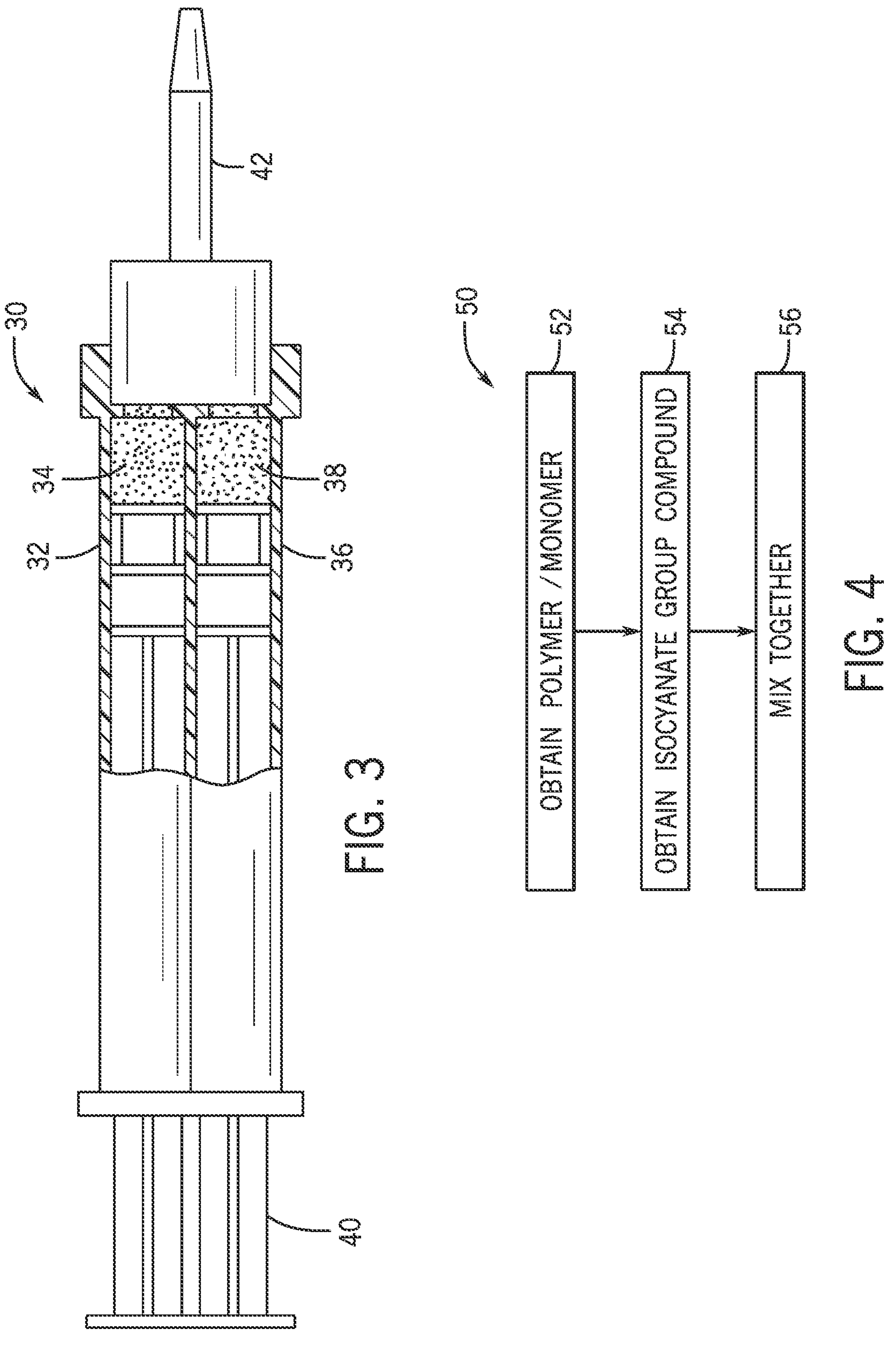
FIG. 3 shows a schematic view of a multi-barrel syringe containing embodiments of a first fluid and a second fluid contained in respective barrels.
FIG. 4 shows a flowchart for a process according to an embodiment.

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

FIGS. 1A and 1B show exemplary views of a tooth 10 having complex and irregular patterns of tooth root canal spaces 12 according to an embodiment. Tooth root canal spaces 12 may have very complex structures and irregular patterns, as they can include main canals 14 and accessory canals 16. Thus, cleaning, disinfecting and filling such irregular patterns may pose difficulties. In an embodiment, a filling material 18 comprises at least one expandable material. The at least one expandable material of the filling material 18 may include at least one of: a swellable material, a foamable material, the like, or any combination thereof. In some embodiments, the expandable material of the filling material 18 may be a crosslinkable material that expands upon crosslinking. In some embodiments, the crosslinking may be performed in situ. In an embodiment, the filling material 18 is configured to expand so as to fill most, substantially all of, or all of the main canals 14 and accessory canals 16 of tooth root canal spaces 12. In an embodiment, the filling material 18 comprises at least one biocompatible material. In an embodiment, the at least one at least one biocompatible material is an expandable material.

FIG. 2 shows a schematic view of an embodiment of a filled or obturated root canal space 12 showing main and accessory canals 14, 16 being filled with the filling material 18.

In some embodiments the expandable material of the filling material 18 expands using isocyanate chemistry (i.e., the chemistry of a material that includes at least one isocyanate group). For instance, in one embodiment, the isocyanate chemistry may be utilized to induce cross-linking of the expandable material of the filling material 18. In one embodiment, the isocyanate chemistry may be utilized to induce foaming of the expandable material of the filling material 18.

Materials including isocyanate groups can become unstable when exposed to various conditions including, but not limited to: the presence of, water, the presence of moisture, the presence of other compounds, and the like. Therefore, various conditions can lead to the decomposition of the isocyanate groups, thereby cross-linking one or more polymers to which the isocyanate groups are attached and releasing carbon dioxide ($CO_2$) gas.

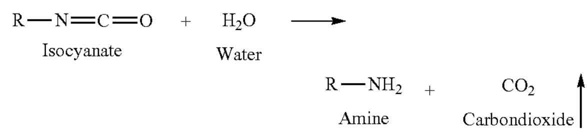

The $CO_2$ gas that is released form pores in some embodiments. In some embodiments, the production or releasing of the $CO_2$ gas is controlled, thereby controlling the formations of the pores in the biocompatible cross-linked polymers. By controlling the production or releasing of the $CO_2$ gas, the three-dimensional structure and thereby its physical properties (such as for example, compression and/or expansion properties) are also controlled to a specific and desired amount. Further, the controlling of the $CO_2$ gas that are exposed to nearby tissue can beneficially minimize the pH change effect in the tissue.

For example, physiologically normal intracellular pH is most commonly between 7.0 and 7.4, though there is variability between tissues (e.g., mammalian skeletal muscle tends to have a pH of 6.8-7.1). Generally, dental infections have some infected tissue which has acidic pH. For example, the pH of pus from a periapical abscess of infected tissue can have a range between 6.0 and 7.3. Therefore, a biocompatible material that does not alter the surrounding tissue pH can be beneficial and advantageous. The embodiments of the biocompatible polymers disclosed herein can be configured to (e.g., controlled) to release low amount of $CO_2$ (e.g., less than 7% of weight). Accordingly, the embodiments of the biocompatible polymers and methods disclosed herein have substantial benefits and advantages over conventional materials and methods.

A non-limiting exemplary mechanism by which a material containing an isocyanate group is crosslinked is shown below. The nonlimiting exemplary mechanism below may be referred to as the "lysine model" of isocyanate crosslinking.

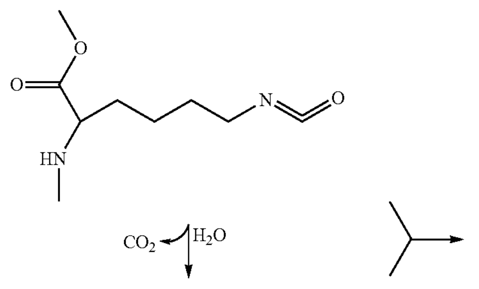

-continued

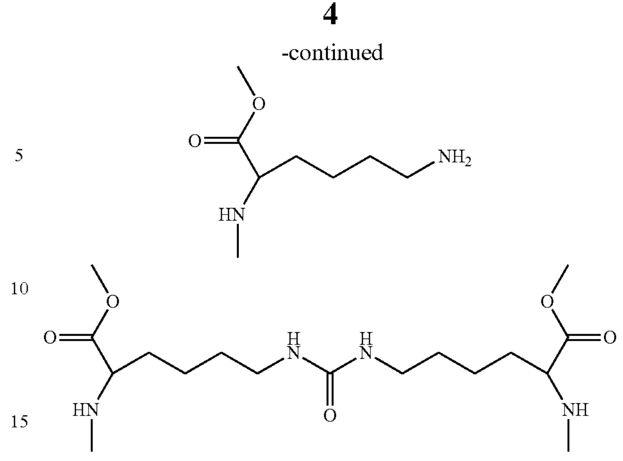

In an embodiment, the filling material 18 includes multiple expandable materials. In some embodiments, the multiple expandable materials are configured to expand upon cross-linking. In an embodiment, the use of multiple expandable materials ensures that the filling material 18 is stable in water and saline.

In an embodiment, an expandable material of the filling material 18 comprises at least one condensation polymer. In an embodiment, the at least one condensation polymer comprises poly glycerol-sebacate ("PGS"). In an embodiment, the at least one condensation polymer is formed by the condensation polymerization of glycerol and sebacic acid. A non-limiting exemplary synthesis pathway by which glycerol and sebacic acid are reacted by condensation polymerization to form PGS is shown below:

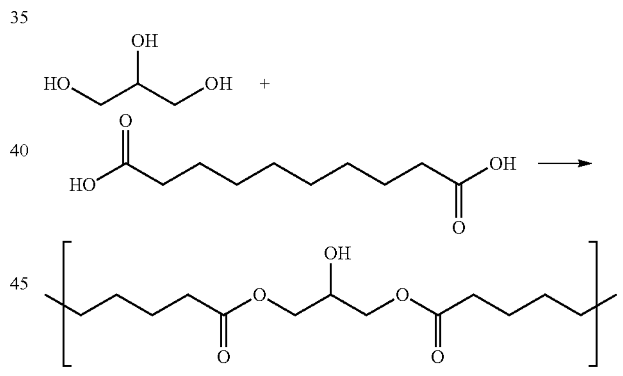

In an embodiment, a polymer of the expandable material of the filling material 18 comprises at least one of: poly (lactic acid) (PLA), poly (glycolic acid) (PGA), at least one polymer from the polycaprolactone (PCL) class of polymers and their copolymers (e.g., poly (lactate-co-caprolactone) or poly (glycolate-caprolactone)), or any combination thereof. In an embodiment, copolymerization of at least one lactide, glycolide, or caprolactone monomer present on at least one polymer of the expandable material of the filling material 18 described herein, in various ratios, can yield materials with a wide range of mechanical properties, thermal characteristics and degradation times. In an embodiment, a structure of an exemplary PLA/PGA/PCL copolymer (and associated properties such as molecular weight) can be tailored by adjusting, for example, a type of initiator used, a molar ratio of the initiator to the at least one monomer unit, or any combination thereof.

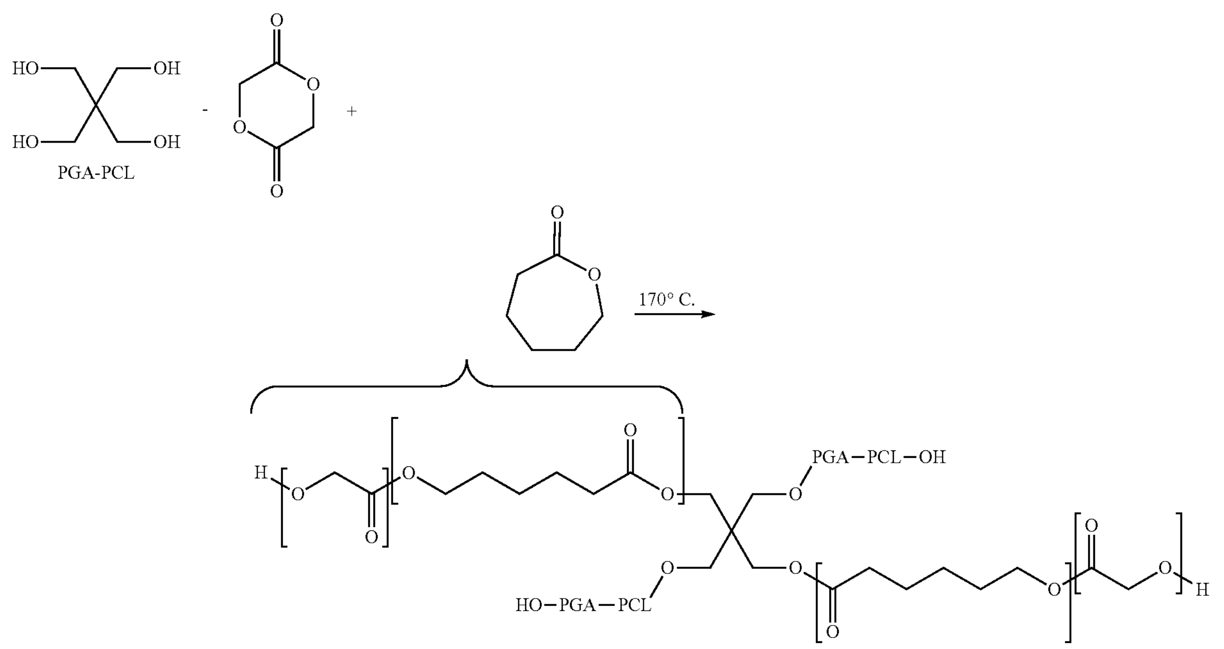

A non-limiting synthesis pathway for poly(glycolide-co-caprolactone) (PGCL) according to one exemplary embodiment is shown below. In the non-limiting pathway below, pentaerythritol is used as an initiator to form 4-armed, branched structures.

In an embodiment, the at least one polymer of the expandable material of the filling material 18 (or the compounds used to make the polymer of the expandable material of the filling material 18) may comprise one or more pendant hydroxyl groups. In an embodiment, the hydroxyl groups may serve, for example, as sites at which pendant groups are attached to the at least one polymer. In an embodiment, glycerol and sebacic acid both contain pendant hydroxyl groups that may be used to impart a desired functionality to PGS. In an embodiment, the filling material 18 may include at least one radiopaque material. In an embodiment, the at least one radiopaque material may include at least one of the following: gold, platinum, tungsten, platinum-tungsten, palladium, iridium, platinum-iridium, rhodium, tantalum, barium sulfate, bismuth subcarbonate, bismuth oxychloride, bismuth trioxide, the like (e.g., a radiopaque metal, a radiopaque alloy, or a radiopaque ceramic), or any combination thereof.

In an embodiment, the filling material 18 may include at least one biostable material. In an embodiment, the at least one biostable material prevents the degradation of the filling material 18 by one or more endogenous enzymes. In a non-limiting exemplary embodiment, the biostable material includes at least one biostable metal oxide, such as for example but not limited to one or more of titanium oxide, ruthenium oxide, and iridium oxide.

In an embodiment, porous polyurethane scaffolds are synthesized when the (PCLG) triol and isocyanate react, with $CO_2$ acting as a blowing agent to create pores.

In an embodiment, at least one expandable material of the filling material 18 comprises at least one polymer foam. In some embodiments, the polymer foam incudes a polymer material including a compound of Formula [A]:

[A]

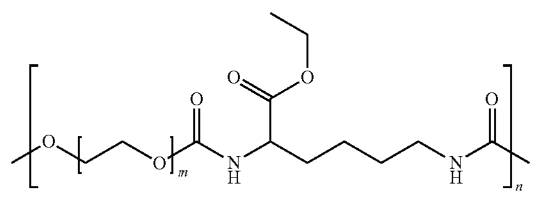

According to an embodiment, a compound of Formula [B] can be prepared and be mixed with a compound of Formula [C]:

[B]

[C]

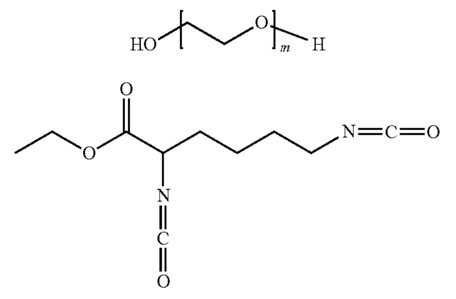

The mixing of the compound [B] and compound [C] leads to polymerization to form the compound of Formula [A]. In an embodiment, the material that includes the compound of Formula [A] has a density of 0.10-0.40 g/cm$^3$.

In some embodiments, a number of units "m" in the polymer comprising the Formula [A] is an integer in a range of 1 to 100 million.

In some embodiments, a number of monomer units "n" in the polymer comprising the Formula [A] is an integer in a range of 2 to 100 million. In some embodiments, the number of monomer units "n" in the polymer comprising the Formula [A] is an integer in a range of 2 to 50 million. In some embodiments, the number of monomer units "n" in the polymer comprising the Formula [A] is an integer in a range of 2 to 10 million. In some embodiments, the number of monomer units "n" in the polymer comprising the Formula [A] is an integer in a range of 2 to 5 million. In some embodiments, the number of monomer units "n" in the polymer comprising the Formula [A] is an integer in a range of 2 to 1 million. In some embodiments, the number of monomer units "n" in the polymer comprising the Formula [A] is an integer in a range of 2 to 100,000. In some embodiments, the number of monomer units "n" in the polymer comprising the Formula [A] is an integer in a range of 2 to 10,000. In some embodiments, the number of monomer units "n" in the polymer comprising the Formula [A] is an integer in a range of 2 to 1000. In some embodiments, the number of monomer units "n" in the polymer comprising the Formula [A] is an integer in a range of 2 to 500. In some embodiments, the number of monomer units "n" in the polymer comprising the Formula [A] is an integer in a range of 2 to 100.

In some embodiments, the number of monomer units "n" in the polymer comprising the Formula [A] is an integer in a range of 100 to 100 million. In some embodiments, the number of monomer units "n" in the polymer comprising the Formula [A] is an integer in a range of 1000 to 100 million. In some embodiments, the number of monomer units "n" in the polymer comprising the Formula [A] is an integer in a range of 10,000 to 100 million. In some embodiments, the number of monomer units "n" in the polymer comprising the Formula [A] is an integer in a range of 10,000 to 100 million. In some embodiments, the number of monomer units "n" in the polymer comprising the Formula [A] is an integer in a range of 1 million to 100 million. In some embodiments, the number of monomer units "n" in the polymer comprising the Formula [A] is an integer in a range of 10 million to 100 million. In some embodiments, the number of monomer units "n" in the polymer comprising the Formula [A] is an integer in a range of 50 million to 100 million.

An exemplary but not necessarily limiting synthesis protocols are provided below.

Example Synthesis 1: Synthesis of High Expandable (HE) (Single-Component Expandable) Polyurethane (PU)

To remove water, polyols, and the chain extender, the sample is heated in a vacuum oven at, for example, 80° C. for 4 hours.

PU polymer: 1 mmol of pre-dried poly(ethylene glycol) (PEG) 400 (0.400 g=357 μL) (kept over a molecular sieve to remove water), and pentamethylguanidine (PMG) (0.031 g) (0.5 wt %, with respect to the reactant), used as a catalyst at around temperature range of 10-40° C. in the polymerization process are taken.

Other fillers for improvement of the integrity and radiopacity may be added, such as for example but not limited to, nano zinc oxide, zirconium oxide nanoparticles, nano calcium tungstate (e.g., 25 weight percentage 0.155 g) and mixed at room temperature (or at a temperature range of 10-40° C.). 1 mmol of L-lysine diisocyanate ethyl ester (LDI) (0.226 g=202 μL) is then added to the mixture.

The freshly prepared PU sealer is a viscous liquid and has injectable properties for dental application. It can also be freshly coated on guttapercha or other types of fillers. The sealer cured slowly for several minutes (up to 180 mins), demonstrating an increase in its viscosity and the degree of cross-linking. Finally, the sealer is cured to form a solid substance.

Example Synthesis 2: Synthesis of High Expandable (HE) (Single-Component Expandable) Polyurethane (PU)

This composite is composed of thermoplastic polyurethane (TPU) as well as some fillers including nano zinc oxide (ZnO) (100 nm). Polyurethane materials are synthesized from diisocyanate and polyalcohol precursors via a condensation reaction. A vast range of required properties is achievable through a suitable choice of the diisocyanates and diols combined in their synthesis.

1. Sealer Base: The pre-dried PEG 400 (CAS Number 253222-68-3) Sigma-Aldrich; LD50=28,000 mg/Kg (oral, rat); hydroxyl value 267-295) (4 g) and l-lysine ethyl ester diisocyanate (LDI) (CAS Number 45172) (7.6 g) are charged into a three-neck flask (Sigma product Number Z418641 equipped with a condenser (Pyrex® West condenser Sigma product Number=CLS270514) a nitrogen inlet/outlet, a thermometer, and a magnetic stirrer at a molar ratio of 1:1.75 (hydroxyl/isocyanate) (hydroxyl Number calculated based on ASTM E1899, EN 15168 and DIN 53240-3). The flask is heated to 60° C. for 4 hours under an $N_2$ atmosphere, and a small amount of 1,4-butanediol (1/10 of LDI) as a chain extender is added to the reaction system for 1 hour to produce the isocyanate (NCO)-terminated PU prepolymer (pre-PPU). Some fillers including Nano Zinc oxide (ZnO) (100 nm particle size CAS Number 1314-13-2), Zirconium Oxide Nanopowder (CAS #: 1314-23-4), Nano calcium tungstate 150 nanometers (CAS Number: 7790-75-2), are added as 25 weight percentage before stirring (for homogenous mixing is better to add the nanoparticle to the prepolymer).

2. Catalyst: Pentamethylguanidine (PMG) is used as a catalyst in the polymerization process.

3. Polymeric sealer: In this example, the sealer includes a polymeric sealer prepared by mixing the Sealer Base and Catalyst in a mass ratio of 10:1 at around temperature of, for example, 10-40° C. The freshly prepared sealer is a viscous liquid with presented injectable properties. The sealer cured slowly. The initial setting time is 15-20 minutes and the final setting time is 4-5 hours which is achieved through the increase of the cross-linking degree and viscosity. Finally, the Polyurethane Expandable sealer is cured as solid and biocompatible (the evaluations of the sealers in terms of their cytotoxicity and preparation of test specimens are performed according to ISO 10993-5 Section (2)).

Example Synthesis 3: Synthesis of PU, Control Expansion (CE) OR Prepolymer Expandable Polyurethane For applications that require a controlled expansion of the biocompatible material, in this embodiment, a prepolymer polyurethane is used to control the polymer's level of expansion.

1. Main Component: The pre-dried PEG (10 mmol 4.00 g=3.57 mL) and LDI (3.96 g=3.54 mL) are charged into a three-neck flask equipped with a nitrogen inlet/outlet, a thermometer, and a magnetic stirrer at a molar ratio of 1:1.75 (hydroxyl/isocyanate). The flask is heated to 60° C. for 4 hours under an $N_2$ atmosphere, and a small amount of 1,4-butanediol (0.16 g=0.157 mL) (1/10 of LDI) is added to the reaction system as a chain extender for 1 hour to produce the isocyanate (NCO)-terminated PU prepolymer (pre-PPU) of Formula [D]:

[D]

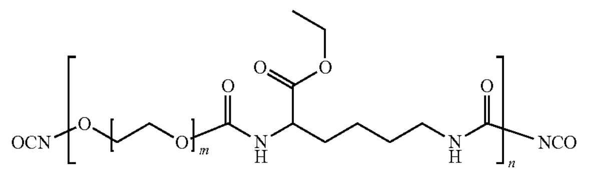

In some embodiments, a number of units "m" in the polymer comprising the Formula [D] is an integer in a range of 1 to 100 million.

In some embodiments, a number of monomer units "n" in the polymer comprising the Formula [D] is an integer in a range of 2 to 100 million. In some embodiments, the number of monomer units "n" in the polymer comprising the Formula [D] is an integer in a range of 2 to 50 million. In some embodiments, the number of monomer units "n" in the polymer comprising the Formula [D] is an integer in a range of 2 to 10 million. In some embodiments, the number of monomer units "n" in the polymer comprising the Formula [D] is an integer in a range of 2 to 5 million. In some embodiments, the number of monomer units "n" in the polymer comprising the Formula [D] is an integer in a range of 2 to 1 million. In some embodiments, the number of monomer units "n" in the polymer comprising the Formula [D] is an integer in a range of 2 to 100,000. In some embodiments, the number of monomer units "n" in the polymer comprising the Formula [D] is an integer in a range of 2 to 10,000. In some embodiments, the number of monomer units "n" in the polymer comprising the Formula [D] is an integer in a range of 2 to 1000. In some embodiments, the number of monomer units "n" in the polymer comprising the Formula [D] is an integer in a range of 2 to 500. In some embodiments, the number of monomer units "n" in the polymer comprising the Formula [D] is an integer in a range of 2 to 100.

In some embodiments, the number of monomer units "n" in the polymer comprising the Formula [D] is an integer in a range of 100 to 100 million. In some embodiments, the number of monomer units "n" in the polymer comprising the Formula [D] is an integer in a range of 1000 to 100 million. In some embodiments, the number of monomer units "n" in the polymer comprising the Formula [D] is an integer in a range of 10,000 to 100 million. In some embodiments, the number of monomer units "n" in the polymer comprising the Formula [D] is an integer in a range of 10,000 to 100 million. In some embodiments, the number of monomer units "n" in the polymer comprising the Formula [D] is an integer in a range of 1 million to 100 million. In some embodiments, the number of monomer units "n" in the polymer comprising the Formula [D] is an integer in a range of 10 million to 100 million. In some embodiments, the number of monomer units "n" in the polymer comprising the Formula [D] is an integer in a range of 50 million to 100 million.

The obtained prepolymer has a lower isocyanate group content, thus decreasing the isocyanate group content, decreases the carbon dioxide production and the expansion of final product.

2. Catalyst B: The glycerol (0.96 g=1.15 mL) is used as a crosslinking agent (i.e., a chain extending catalyst). Pentamethylguanidine (PMG) (0.062 g), and other fillers (nano zinc oxide, zirconium oxide nanoparticles, or nano calcium tungstate (0.9 g)) are added, and the mixture is used as a catalyst in the polymerization process. The above pre-dried agents are mixed and served as catalyst B.

3. PU polymeric sealer: The PU polymeric sealer is prepared by mixing the pre-PPU with catalyst B at around, for example, a temperature range of 10-40° C. The freshly prepared PU sealer is a viscous liquid and presented injectable properties. The sealer cured slowly for several minutes, demonstrating an increase in the cross-linking degree and viscosity. Finally, the PU sealer mixture is cured at room temperature (e.g., temperature range from 30-35° C.) to form a solid.

Two-step prepolymer polyurethane allows for the control of the expansion in polyurethane. The expansion ratio is controlled by changing and modifying the PEG and LDI ratio in the main component. Also, changing the PEG molecular weight can change the mechanical properties of the final products. For example, the resulting final product from this synthesis can have a density of 0.15-0.50 g/cm$^3$.

Example Method of Use 1: In an exemplary non-limiting embodiment, the filling material 18 can be prepared in a dental operating room setting by the following steps:

1. Adding a hardener to isocyanate in a sterile canister.
2. Inserting the canister into a fixture loading tray.
3. Lowering an impeller into the canister at a pre-set mixing height.
4. Mixing the isocyanate and hardener mixture in the canister for about 40 seconds at about 11,000 RPM.
5. Withdrawing the shaft from the canister.
6. Removing the canister from loading tray.
7. Injecting polyurethane into the mixed isocyanate and hardener mixture.

Example Method of Use 2: In another exemplary non-limiting embodiment, the filling material 18 can be prepared in a dental operating room setting by the following steps:

1. Adding a hardener to isocyanate in a sterile canister.
2. Inserting the canister into a fixture loading tray.
3. Lowering an impeller into the canister at a pre-set mixing height.
4. Mixing the isocyanate and hardener mixture in the canister for 30-50 seconds at 10,000 to 12,000 RPM. For example, mixing the isocyanate and hardener mixture in the canister for 40 seconds at 11,000 RPM.
5. Withdrawing the shaft from the canister.
6. Removing the canister from loading tray.
7. Injecting biopolymer into the isocyanate and hardener mixture.

In an embodiment, the resulting mixture results in middle or low level porous and biocompatible biopolymers that can be use as the root filing material 18.

FIG. 3 shows a nonlimiting exemplary embodiment of a multi-barrel syringe 30 (e.g., a double barrel syringe) comprising a first barrel chamber 32 containing a first fluid 34, and a second barrel chamber 36 containing a second fluid 38.

In an embodiment, the first fluid 34 includes the compound of Formula [B] according to the above, and the second fluid 38 includes the compound of Formula [C] according to the above.

In another embodiment, the first fluid 34 includes the prepolymer of Formula [D] according to the above, and the second fluid 38 includes a crosslinking agent (i.e., a chain extending catalyst), such as for example, glycerol.

When the plunger(s) 40 of the multi-barrel syringe 30 is(are) pressed, the pressure forces the first fluid 34 and the second fluid 38 to flow downstream. At or near the tip 42 of the multi-barrel syringe 30, the first fluid 34 and the second fluid 38 are mixed together.

According to an embodiment, the first fluid 34 and the second fluid 38 are mixed together the outside of the multi-barrel syringe 30.

According to an embodiment, the first fluid 34 and the second fluid 38 are mixed together downstream of the first barrel chamber 32 and the second barrel chamber 36 of the multi-barrel syringe 30.

According to an embodiment, the mixing together of the first liquid 34 and the second liquid 38 is not outside of the multi-barrel syringe 30.

According to an embodiment, the tip 42 is a mixing tip 42, which may or may not be a separable component, and the first fluid 34 and the second fluid 38 are mixed together as they flow through the mixing tip 42.

FIG. 4 shows a nonlimiting exemplary embodiment of a method 50 of producing an expandable biocompatible polymer material. In the first step 52, at least one polymer is obtained, wherein the at least one polymer comprises at least one monomer unit or a prepolymer such as for example one or more chosen from: at least one lactide unit, at least one glycolide unit, at least one caprolactone unit, or any combination thereof. In the second step 54, at least one compound comprising at least one isocyanate group is obtained.

According to an embodiment, in the first step 52, the monomer unit is a compound of Formula [B] and in the second step 54, the compound includes that of Formula [C].

According to an embodiment, in the first step 52, the prepolymer is a compound of Formula [D] and in the second step 54, the compound includes a crosslinking agent (i.e., a chain extending catalyst), such as for example, glycerol.

In the next step 56, the at least one polymer with the at least one at least one compound comprising the at least one isocyanate group are mixed together such that they react to form a biocompatible polymer material. The biocompatible polymer material can be used to fill at least one portion of a cavity or an empty space, such as for example, a tooth or a tooth canal.

In some embodiments of the methods for making the polymer material, the method does not include using a surfactant. That is, the process of making the polymer material does not require any surfactant. Examples of the surfactants include, but are not necessarily limited to one or more of the following: silane, sodium lauryl sulphate (SLS), cocamidopropyl betaine (tego betain) and sodium methyl cocoyl taurate (adinol). In some embodiments of the methods for making the polymer material, the method does not include using an additive bonding agent. That is, the process of making the polymer material does not require any additive bonding agent. Examples of the bonding agents include, but are not necessarily limited to one or more of an adhesive, an epoxy, a resin, or acetone. In some embodiments of the methods for making the polymer material, the method does not include using both of the surfactant and the bonding agent.

The following aspects are provided as exemplary embodiments of the present disclosure.

Aspect 1. A composition comprising:

at least one polymer, wherein the at least one polymer comprises at least one monomer unit chosen from: at least one lactide unit, at least one glycolide unit, at least one caprolactone unit, or any combination thereof; and at least one compound comprising at least one isocyanate group.

Aspect 2. A method comprising:

obtaining at least one polymer, wherein the at least one polymer comprises at least one monomer unit chosen from: at least one lactide unit, at least one glycolide unit, at least one caprolactone unit, or any combination thereof;

obtaining at least one at least one compound comprising at least one isocyanate group;

reacting the at least one polymer with the at least one at least one compound comprising the at least one isocyanate group so as to form a biocompatible material; and filling at least one portion of at least one tooth with the biocompatible material.

Aspect 3. A composition comprising:

a polymer material including a compound of Formula [A]:

[A]

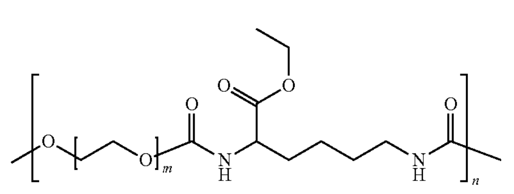

wherein:

m is 1 to 100 million; and n is 2 to 100 million.

Aspect 4. A method for making a polymer material, comprising:

mixing a compound of Formula [B] with a compound of Formula [C]:

[B]

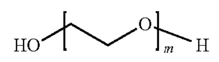

[C]

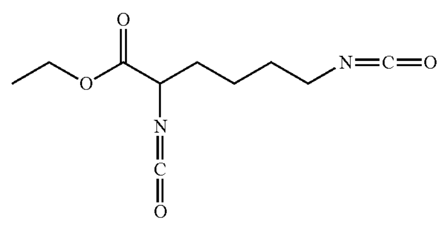

to polymerize the compound of Formula [B] with the compound of Formula [C] and producing a compound of Formula [A]:

[A]

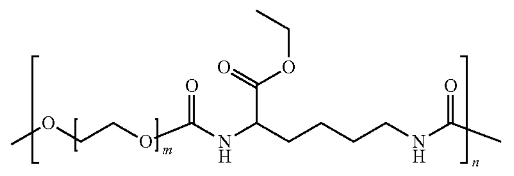

wherein:

m is 1 to 100 million; and n is 2 to 100 million.

Aspect 5. A composition comprising:

a polymer material obtained by polymerizing a prepolymer of Formula [D] with a chain extending catalyst:

[D]

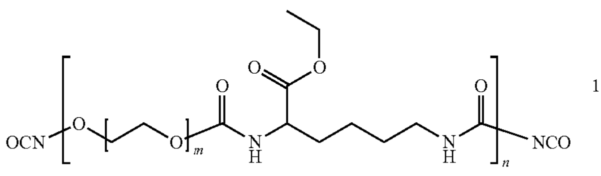

wherein:

m is 1 to 100 million; and n is 2 to 100 million.

Aspect 6. The composition according to Aspect 5, wherein the chain extending catalyst includes glycerol.

Aspect 7. A method for making a polymer material, comprising:

mixing a prepolymer of Formula [D] with a chain extending catalyst:

[D]

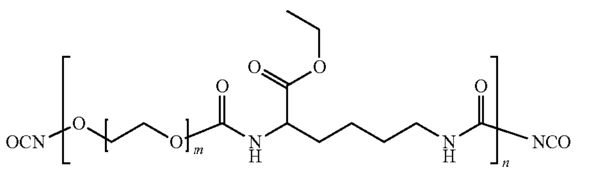

wherein:

m is 1 to 100 million; and n is 2 to 100 million.

Aspect 8. The method according to Aspect 7, wherein the chain extending catalyst includes glycerol.

Aspect 9. A multi-barrel syringe comprising:

a first barrel containing a first liquid compound including a poly(ethylene glycol) of Formula [B]; and a second barrel containing a second liquid compound including a L-lysine disocyanate ethyl ester of Formula [C]:

[B]

[C]

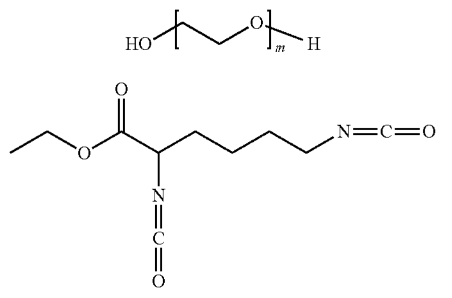

wherein:

m is 1 to 100 million.

Aspect 10. A method comprising:

obtaining a multi-barrel syringe including a first barrel containing a first liquid compound including a poly (ethylene glycol) of Formula [A], and a second barrel containing a second liquid compound including a L-lysine disocyanate ethyl ester of Formula [B];

applying pressure to the first barrel such that the first liquid is pressed downstream of the first barrel;

applying pressure to the second barrel such that the second liquid is pressed downstream of the second barrel; and mixing together the first liquid and the second liquid downstream of the multi-barrels syringe.

Aspect 11. The method of Aspect 10, further comprising:

obtaining a polymer material including a compound of Formula [A]:

[A]

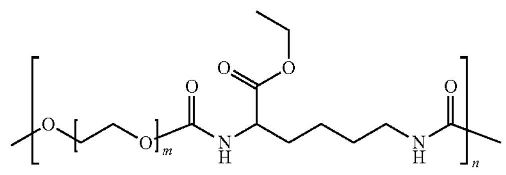

wherein:

m is 1 to 100 million; and n is 2 to 100 million.

Aspect 12. The method according to Aspect 10, wherein the mixing together of the first liquid and the second liquid is downstream and outside of the multi-barrel syringe.

Aspect 13. The method according to Aspect 10, wherein the mixing together of the first liquid and the second liquid is downstream of the first barrel and the second barrel of the multi-barrel syringe.

Aspect 14. The method according to Aspect 13, wherein the mixing together of the first liquid and the second liquid is not outside of the multi-barrel syringe.

Aspect 15. The method(s) according to any one or more of Aspects 2, 4, 7, 8, and 10-14, wherein the method does not include using a surfactant.

Aspect 16. The method according to Aspect 15, wherein the method does not include using an additive bonding agent.

Aspect 17. Any one or more of the Aspects 2, 4, 7, 8, and 10-14, wherein the method does not include using an additive bonding agent.

What is claimed is:

1. A composition, comprising:

a polymer foam material including a compound of Formula [A]:

[A]

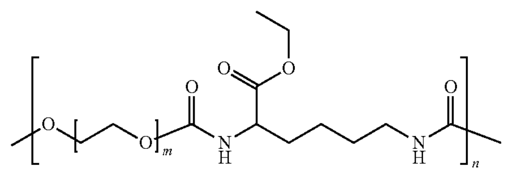

wherein:

m is 1 to 100 million, and n is 2 to 100 million;

a radiopaque material, wherein the radiopaque material excludes barium sulfate and comprises at least one of platinum, tungsten, platinum-iridium, tantalum, bismuth oxychloride, or bismuth trioxide; and a biostable material, wherein the biostable material comprises at least one biostable metal oxide.

2. A method for making the composition of claim 1, comprising:

mixing a compound of Formula [B] with a compound of Formula [C]:

[B]

[C]

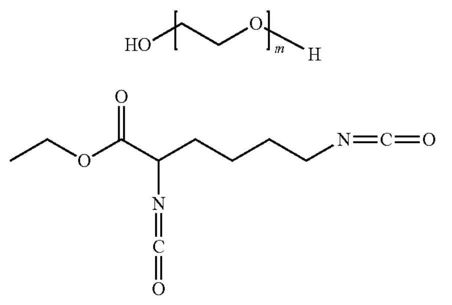

to polymerize the compound of Formula [B] with the compound of Formula [C] and producing the compound of Formula [A];

inducing foaming of the compound of Formula [A]; and mixing the radiopaque material and the biostable material to form the composition of claim 1.

3. The composition of claim 1, wherein the polymer foam material has a density of 0.1 to 0.4 $g/cm^3$.

4. The composition of claim 1, wherein the biostable material is configured to prevent degradation of the polymer foam material.

5. The composition of claim 1, wherein the biostable oxide comprises one or more of titanium oxide, ruthenium oxide, and iridium oxide.

* * * * *